United States Patent [19]

Wagner et al.

[11] Patent Number: 5,449,786
[45] Date of Patent: Sep. 12, 1995

[54] METHOD FOR THE CHEMICAL RACEMIZATION OF 5-MONOSUBSTITUTED HYDANTOINS BY CONTACT WITH ANIONIC ION EXCHANGER

[75] Inventors: Fritz Wagner, Braunschweig; Christoph Syldatk, Hildesheim; Markus Pietzsch, Braunschweig, all of Germany

[73] Assignee: Degussa Aktiengesellschaft, Frankfurt am Main, Germany

[21] Appl. No.: 975,170

[22] Filed: Nov. 16, 1992

[30] Foreign Application Priority Data

Nov. 15, 1991 [DE] Germany .................. 41 37 581.5

[51] Int. Cl.$^6$ .................. C07D 403/06; C07D 233/76; C07D 233/74; C07D 209/20
[52] U.S. Cl. .................. 548/312.1; 548/317.1
[58] Field of Search .................. 548/317.1, 312.1

[56] References Cited

U.S. PATENT DOCUMENTS 4,647,694  3/1987  Hosztafi et al. .................. 562/443

FOREIGN PATENT DOCUMENTS

| 60-25972 | 2/1985 | Japan | 548/317.1 |
| 60-202867 | 10/1985 | Japan | 548/317.1 |
| 90188025 | 6/1991 | Japan | 548/317.1 |
| WO91/08196 | 6/1991 | WIPO | 548/317.1 |

OTHER PUBLICATIONS

Barrett, Amino Acids and Peptides, vol. 20, pp. 1 to 61 (1989).
Belokon et al., Makromol. Chem., vol. 187, pp. 1065 to 1067 (1986).
Dudley et al., Chemical Abstracts, vol. 85, #192096K (1976).
Lazarus, J. Org. Chem., vol. 55, pp. 4755 to 4757 (1990).
Vogels et al., Recl. Trav. Chim. Pays-Bas, vol. 88, pp. 940 to 950 (1969).
Syldatk et al., J. of Biotechnology, vol. 14, pp. 345 to 362 (1990).
Ware, Chem. Rev., vol. 46, pp. 449 to 453 (1950).
Yokozeki et al., Agric. Biol. Chem., vol. 51, pp. 721 to 728 (1987).
Amer. Chem. J., vol. 44, pp. 43 to 60 (1910) Dakin.
Sobotka, J. Amer. Chem. Soc., vol. 54, pp. 4697 to 4702 (1932).
Smith et al., J. Org. Chem., vol. 22, pp. 442 to 444 (1957).

*Primary Examiner*—Floyd D. Higel
*Attorney, Agent, or Firm*—Cushman Darby & Cushman

[57] ABSTRACT

A method for the racemization of 5-monosubstituted hydantoins, in which a 5-monosubstituted hydantoin is reacted in the presence of an ion exchanger. Anion exchangers at a pH between 6.0 and 13.5 are preferred.

7 Claims, 2 Drawing Sheets

METHOD FOR THE CHEMICAL RACEMIZATION OF 5-MONOSUBSTITUTED HYDANTOINS BY CONTACT WITH ANIONIC ION EXCHANGER

The present invention relates to a method for the racemization of 5-monosubstituted hydantoins, apparatus for carrying out that method and the use of the racemized hydantoins.

BACKGROUND OF THE INVENTION

The racemates produced in the chemical synthesis of amino acids are usually separated into the individual enantiomers by enzymatic splitting. This can be carried out e.g. by stereospecific enzymatic splitting of the N-acylated amino acids or by enantioselective enzymatic splitting of the corresponding hydantoins which are monosubstituted in 5-position. In each case, an unsplit enantiomer of the starting material can be recovered and subjected once again, after a racemization process, to enzymatic splitting. A good survey of possible racemizations is provided by E. Adams in P. D. Boyer, "The Enzymes", vol. VI, New York, 1972, pp. 479–507 (Amino Acid Racemases and Epimerases). In principle, the racemization process can be carried out chemically, physico-chemically or enzymatically. Combined methods are also possible, depending on process conditions. An enzymatic hydantoin racemization is described by M. Pietzsch in "Stereochemische Untersuchungen zur enzymatischen Hydrolyse von D,L-5-monosubstituierten Hydantoinen" [Stereochemical Investigations on the Enzymatic Hydrolysis of D,L-5-Monosubstituted Hydantoins], thesis, Technical University of Braunschweig, 1989, in which a racemase from Arthrobacter spec. (DSM 3747) was used. However, enzymatic methods have the disadvantage that the known racemases have high substrate specificity and therefore can only be used for very special methods. For many hydantoins, no racemases are known yet.

For this reason the chemical or physico-chemical racemization predominates in the case of the hydantoins as well as amino acids. In such racemization the educts are usually subjected to a temperature-time program under basic conditions. Methods are also known for amino acids in which the racemization is carried out on strongly basic anionic exchangers; in those cases, relatively low temperatures (25°–45° C.) are sufficient. However, these anion exchanger methods are only successful in the case of neutral or basic amino acids and require the use of copper(II) ions; in those cases, a reactive copper(II) Schiff's base complex is produced as an intermediate. G. C. Barrett, Amino Acids and Peptides 20, pp. 1–51 (1989) provides a survey of these methods, and special methods are described in Makromol. Chem. 187, pp. 1065–1076 (1986). These methods are extremely expensive and can only be carried out on a laboratory scale since, in addition to the copper ions an ion exchanger neutralized with 4-hydroxy-3-formylbenzene-sulfonic acid (5-sulfosalicylaldehyde) is used. This material requires a regeneration. It also requires an expensive purification of the products obtained, since the copper ions must be removed. quantitatively. Moreover, the use of transition-metal cations has the disadvantage that very stable complexes can possibly be formed with the amino acids used.

The chemical racemization of 5-monosubstituted hydantoins runs via keto-enol tautomerism (Chem. Rev. 46, pp. 403–470 (1950)) and is catalyzed, as was determined very early on, by bases (Am. Chem. J. 44, pp. 48–60 (1910)). More recent investigations on the chemical racemization of hydantoins were carried out only with special substrates, e.g. 5-(p-hydroxyphenyl)-hydantoin in Agric. Biol. Chem. 51, pp. 721–728 (1987) and 5-benzylhydantoin in J. Org. Chem. 55, pp. 4755–57 (1990). These investigations show that a rapid racemization occurs only in the case of 5-(p-hydroxy-phenyl)-hydantoin because of resonance stabilization by the 5-substituent (50% after 20 min.)—all other hydantoins racemize only after several hours.

SUMMARY OF THE INVENTION

The object of the present invention is to provide a method for the racemization of 5-monosubstituted hydantoins in which the racemization can be carried out under mild conditions and is useful with a variety of substrates. A further object is to provide such a method which is as simple as possible to carry out, that is, it should be possible to eliminate undesirable ions, such as, e.g., various transition-metal cations or other compounds which are expensive to remove. Yet another object is to provide such a method in which the racemization can take place in an acceptably short time and with good yields. Still another object is to provide an apparatus suitable for carrying out the method.

These and other objects are achieved by a racemization method in which the enantiomer of a hydantoin which is substituted in 5-position is reacted in the presence of an anion exchanger at a pH in a range of 6–13.5.

The hydantoins used have the general formula

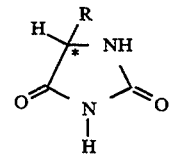

* signifies a center of symmetry at which the racemization takes place and in which R is a group of an amino acid which can be proteinogenic or non-proteinogenic.

Typical R groups are:

Phenyl

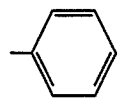

Benzyl

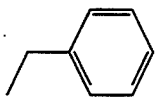

Isopropyl

Methylthioethyl

It is advantageous to subsequently split the racemized hydantoins and react only one of the two enantiomers (as a rule the one obtained again by the racemization). The nonsplit hydantoin enantiomer can subsequently be separated from the L- or D-α-amino acid produced and racemized again. The enzymatic splitting can be carried out by means of free enzymes or in an especially advantageous manner with cellbound enzymes (resting cells). The splitting preferably takes place at 10°–60° C. and optionally under gentle agitation.

The enzymatic splitting can be carried out in a known manner. General enzymatic reactions are described in R. Tsugawa, F. Okumura, T. Ito, Agric. Biol. Chem. 30, p. 27 (1966). The production of D— amino acids is explained in Published European Patent Application EP-A 0,400,638 (90,110,345.7); L-α-amino acids are described by C. Syldatk, V. Mackowiak, H. Hoke, C. Gross, G. Dombach and F. Wagner in J. Biotechnol. 14, p. 345 (1990).

The ion exchanger can be present in gel form, as solid or in liquid or soluble form. Gel-formed and solid ion exchangers can be used, e.g., in fixed-bed reactors whereas liquid or soluble ion exchangers are usually used, e.g., in mixed reactors. In addition to the fixed-bed reactors (e.g. chromatography columns), the gel-formed and solid ion exchangers can also be used in mixed reactors such as e.g. fluid-bed reactors, agitated reactors and ultrafiltration reactors.

The use of anion exchangers in a pH range of 6.0–13.5, preferably 6.5–11 is suitable and in particular strongly basic anion exchangers, e.g. those with quaternary ammonium groups or based on phosphonium, show especially good results. If the pH is too low, no conversion takes place; in the case of too high a pH the hydantoin racemizes even without the presence of the ion exchanger. Ion exchangers with at least partially organic, preferably pure organic structure are preferred because of their low cost.

It is especially useful that, according to the invention, the hydantoin to be racemized can be brought in contact with the ion exchanger in a buffered solution, so that side reactions can be largely avoided. A desired pH can also be adjusted, if necessary, with the buffer system, especially when using a solid ion exchanger. It is advantageous in this connection if the buffer system is selected in such a manner that a subsequent, e.g. enzymatic, splitting of the racemic mixture can be carried out in the same buffer system, optionally with variation of the pH'es. It also is especially advantageous that the racemization can be carried out in a continuous manner on the ion exchanger, since the ion exchanger requires no regeneration. In such a continuous method the hydantoin to be racemized, preferably in a buffered solution, is continuously supplied to a column packed with the ion exchanger, which column is preferably a thermostatted column, especially if the conversion is highly temperature-dependent. The column dimension and the hydantoin through, that is, the flow-through speed of the system at a certain concentration of hydantoin, should be coordinated with one another in such a manner that the hydantoin which has left the column in solution is racemized practically competely. In the case of commercial ion exchangers this usually requires a contact time of substrate and ion exchanger of between 5 min. and 2 hours per ml of ion exchanger at a temperature between approximately 0 and approximately 100° C. (tempering range in the case of aqueous solutions), preferably 20°–70° C. and at a concentration of 0.1–250 g/l, preferably 0.2–50 g/l hydantoin in water or the buffer system.

The method is advantageously carried out in a fixed-bed reactor with a typical chromatographic system, that is, with a column filled with an ion exchanger and in whose inlet the solution of the hydantoin to be racemized is added, preferably in a buffer. The hydantoin can be directly collected at the column outlet or conducted via control measuring devices such as e.g. a polarimeter.

The method of the invention has the important advantages, given its ability to be carried out in an amazingly simple manner, that a plurality of different hydantoins can be racemized with a single ion exchange type which contain aliphatic, charged or otherwise functionalized and/or aromatic substituents in the 5-position. Only in the case of a replacement of the solution should the ion exchanger be equilibrated again in advance with the buffer system. As a rule, a regeneration is not necessary. The method of the invention is equally well-suited for the racemization of D-5- and L-5-substituted hydantoins, so that the method can be used in the production of D- and L- amino acids. Practically any hydantoin can be completely racemized by a suitable selection of the parameters (buffer system, pH, ion exchange material, temperature, flowthrough speed).

It is helpful if the buffer system has a concentration between 0.005 and 1.0 mole/l and concentrations between 0.01 and 0.1 mole/l are advantageous. Suitable systems are e.g. glycine (NaOH), phosphate (K+, Na+), tris (HCl) (tris(hydroxymethyl)-aminomethane), and glycine/NaOH yields especially good conversions.

In principle, the process can also be carried out without an additional buffer system, in which case the pH can be optionally adjusted by addition of an acid (e.g. HCl) or a base (e.g. NaOH) directly to the hydantoin to be racemized. Accompanying substances accumulating with the hydantoin to be racemized can also be included in a buffer system.

Non-functionalized gel material as well as cation exchangers are unsuitable as catalyst (e.g. Sephacryl S-300, a gel filtration medium and Amberlite IR-122, a strongly acidic cation exchanger) and weak ion exchangers are potentially suitable (e.g. of the DEAE type, e.g. DEAE Sepharose), as are heavily shielded (liquid) anion exchangers (e.g. tetrabutylammoniumhydrogen sulfate), since they require considerably greater dwell times of the substrate on the column for a comparable conversion than strong ion exchangers do (e.g. ion exchangers of the Q type, e.g. Q-Sepharose from Pharmacia, Freiburg or Amberlite IRA-410 (hydrophobic polystyrene matrix)).

If racemization is carried out in a basic environment, the racemization speed increases with the pH, with limits being set for the upper pH by the column material and by the stability of the hydantoin. Even elevated temperatures accelerate the racemization speed. Furthermore, the racemization speed is influenced by the molarity of the buffer system used and by the buffer type.

BRIEF DESCRIPTION OF FIGURES OF DRAWINGS

The method of the invention is illustrated in detail by the drawings in which.

DETAILED DESCRIPTION OF PREFERRED EMBODIMENTS

Figure 1:
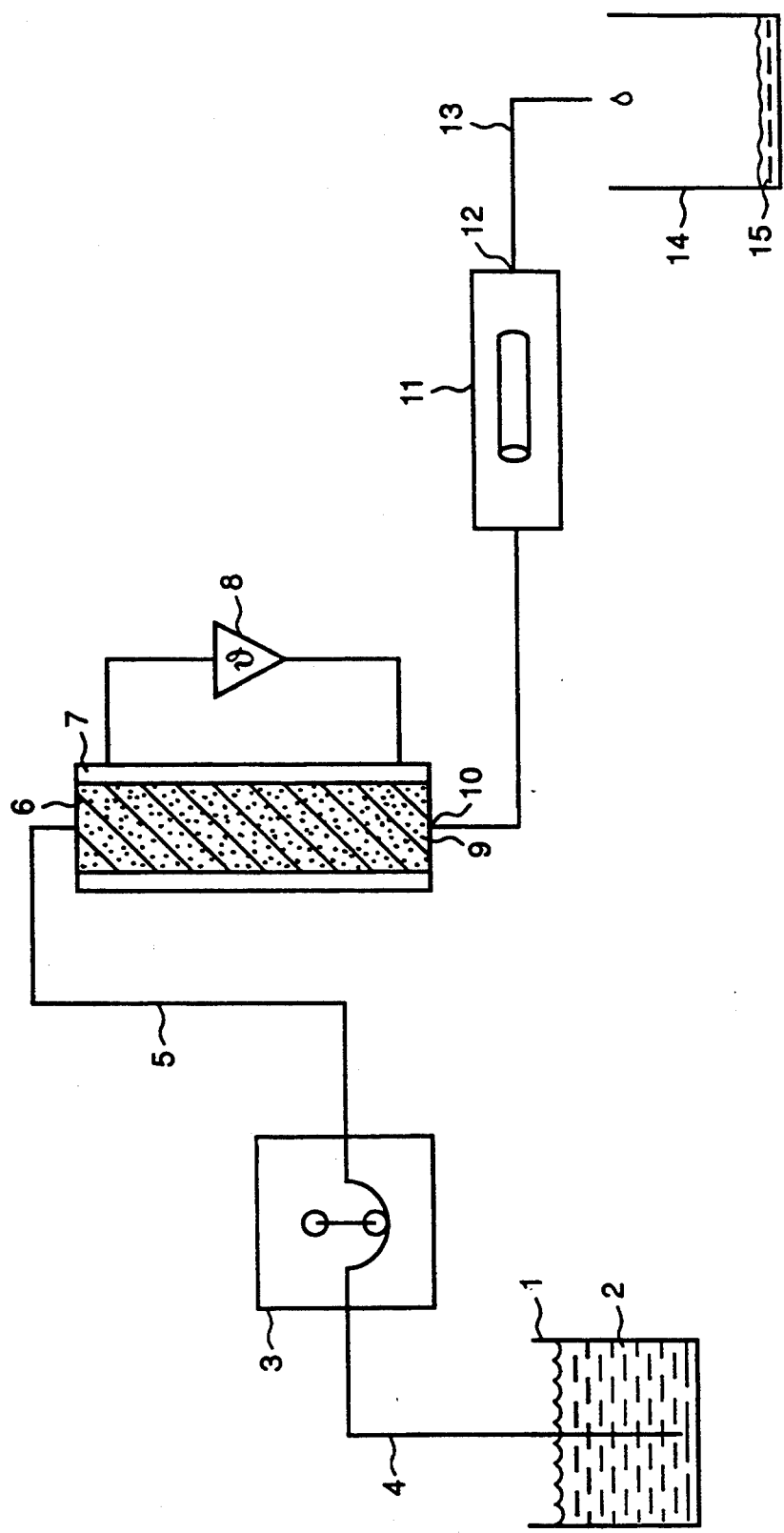
FIG. 1 shows in schematic fashion the design of apparatus for carrying out the method of the invention.

In the apparatus shown in FIG. 1, a solution 2 of the buffer system and of the hydantoin to be racemized is located in a receiver 1. Hose pump 3 sucks solution 2 via line 4 and pumps it via connection 5 onto column 6 which has a temperature-controlled jacket 7 in turn connected to thermostat 8. Column 6 is filled with ion exchanger gel 9. Outlet 10 of column 6 is connected to flowthrough polarimeter 11 whose outlet 12 terminates via line 13 at vessel 14 in which solution 15 with the racemized hydantoin is collected.

Receiver 1 can be charged continuously or discontinuously with accumulating solution 2. For a further control, an autosampler for e.g. HPLC measurements can also be inserted after column 6 or after polarimeter 11. Accumulating solution 15 can also, to the extent desired, be collected in a fraction collector or supplied directly to a further stage for resolution of racemates.

In the following examples a thermostable XK-16/10 column from Pharmacia, Freiburg was used, unless otherwise specified, for column 6, which column was packed with approximately 32 ml degassed anion exchanger, Q-Sepharose fast flow (Pharmacia), at a flow rate of 2.0 ml/min and equilibrated (approximately 200 ml) with the particular buffer system used for the production of the substrate solution.

The conversion given is the percentage of the hydantoin enantiomer which was racemized; for example, a 50% conversion signifies an enantiomeric ratio of 3:1.

EXAMPLE 1

A solution of 0.2 g L-5-indolylmethylhydantoin in 1000 ml 0.05M glycine buffer (Na+, pH 8.5) was used as substrate solution. The column was thermostated at 37° C. and the substrate solution pumped with a flow rate of 0.6 ml/min over the column. The hydantoin was racemized practically completely (>99%) at this and at all lesser flow rates.

EXAMPLE 2

The same procedure was used as in Example 1 except that instead of Q-Sepharose fast flow, DEAE-Sepharose fast flow (Pharmacia) was used. The column was equilibrated with a tris/HCl buffer (0.02M, pH 8.5). A racemization of 92% was obtained at a flow rate of 0.1 ml/min.

Reference example 1

The same procedure was used as in Example 2 except that, instead of DEAE-Sepharose fast flow, Sephacryl S-300 (Pharmacia) was used. No racemization could be observed under the given conditions.

EXAMPLE 3

As described in Example 1, L-5-indolylmethylhydantoin was racemized with a phosphate buffer (0.05M, K+, pH 6.5) being used for the buffer- and substrate solution. A racemization of 6% was achieved at a flow rate of 1.2 ml/min.

EXAMPLE 4

Example 3 was repeated with a phosphate buffer (K+) with a pH of 7.5. A racemization of 42% was achieved at a flowthrough rate of 0.6 ml/min.

EXAMPLE 5

Example 4 was repeated with a phosphate buffer (K+) of pH 8.5. The conversion changed solely due to the variation of the buffer medium in relation to Example 1; a racemization of 64% was achieved under the given conditions.

EXAMPLE 6

Examples 1 and 5 were repeated, except that 0.02M tris/HCl buffer (pH 8.5) was used as buffer- and substrate solution. The conversion of the racemization was 66% at a flow rate of 0.6 ml/min.

EXAMPLE 7

The same procedure was used as in Example 5 except that a solution of 1.0 g D-5-methylthioethylhydantoin in 1000 ml of phosphate buffer was used as substrate solution. The racemization of the substrate takes place with a conversion of 66% at a flow rate of 0.3 ml/min.

EXAMPLE 8

The same procedure was used as in Example 6 except that a solution of 1.0 g L-5-carboxyethylhydantoin in 1000 ml of the buffer was used. A complete racemization of the substrate occurs at a flow rate of 0.3 ml/min and less.

EXAMPLE 9

Example 8 was repeated except that L-5-isopropylhydantoin was used. A racemization of only 10% was achieved.

EXAMPLE 10

Example 9 was repeated at a column temperature of 70° C. with the other conditions remaining the same. A complete racemization of the substrate occurs at this and all higher temperatures.

EXAMPLE 11

Figure 2:
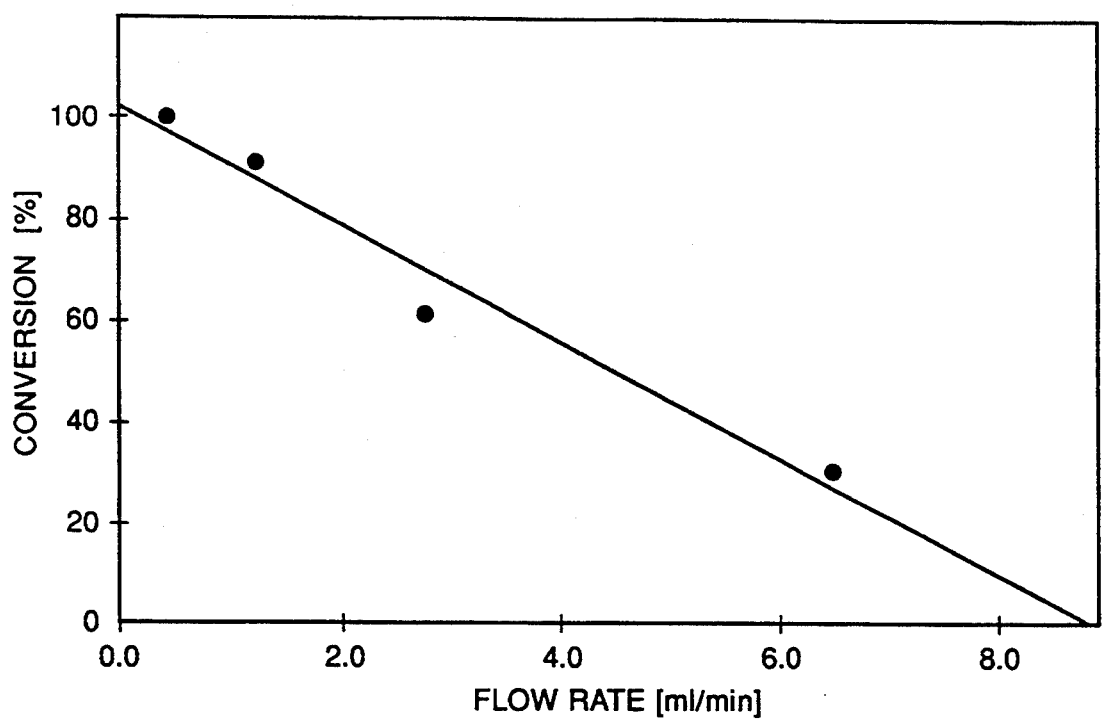
FIG. 2 shows the racemization of D-5-indolylmethylhydantoin (D-5-IMH) on Q-Sepharose as a function of the flow rate.

This example investigated the relationship between the flow rate and the conversion. The result is plotted in FIG. 2. There is a linear connection between the flow rate and the conversion.

A solution of 0.2 g D-5-indolylmethylhydantoin in 1000 ml 0.05M glycine buffer (Na+, pH 8.5) was used as substrate solution. The column (16 ml Q-Sepharose) was thermostated to 37° C. and the substrate solution was pumped through the column at a flow rate of 6.5 ml/min. A racemization of 29.6% was achieved at this flow rate. At flow rates of 2.8 ml/min, 1.25 ml/min and 0.4 ml/min a racemization of 60.8%, 90.3% and approx. 100% was achieved.

EXAMPLE 12

Figure 3:
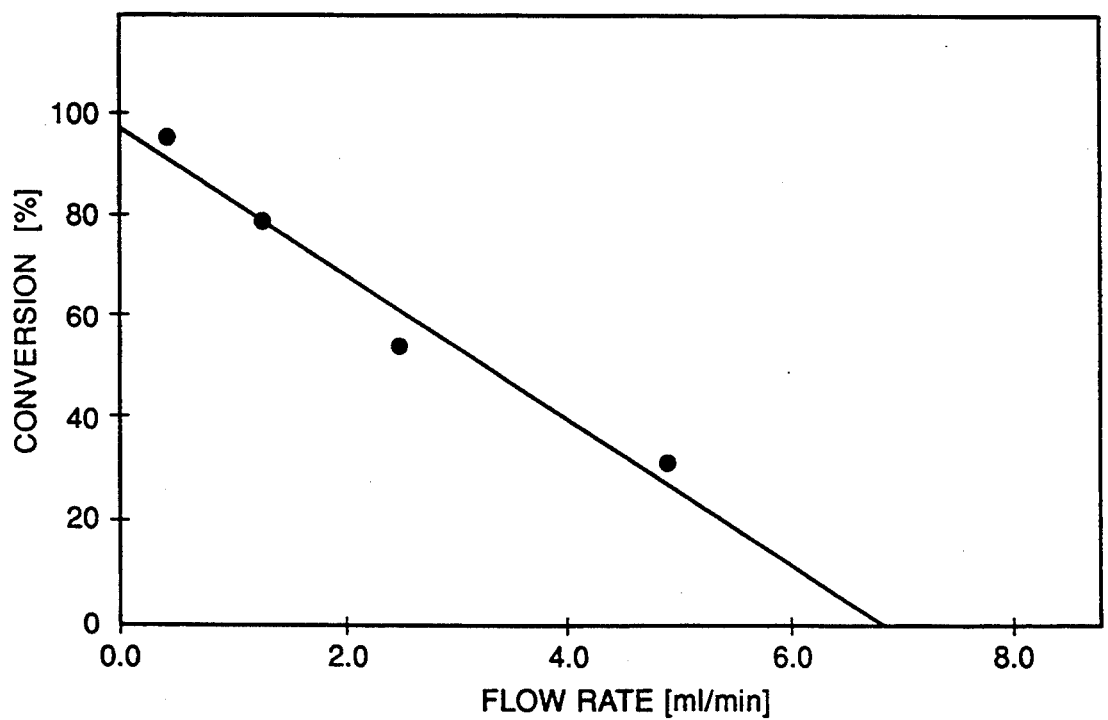
FIG. 3 shows the racemization of D-5-IMH on Amberlite IRA 410 as a function of the flow rate.

This example investigated the suitability of an industrial anion exchanger. As FIG. 3 shows, there is also a linear connection between flow rate and racemization speed (conversion). However, the column material (hydrophobic polystyrene matrix) absorbs distinctly more IMH at first in the equilibration phase than the Q-Sepharose (hydrophilic Sepharose matrix) used above.

The same procedure was used as in Example 11 except that, instead of Q-Sepharose, Amberlite IRA-410 (analytical grade, Serva, Heidelberg, gel volume 5.3 ml) was used. A racemization of 29.7% was achieved at a flow rate of 5.0 ml/min. At a flow rate of 2.5 ml/min, 1.25 ml/min and 0.4 ml/min racemizations of 54.4%, 79.4% and 96% were achieved.

Reference Example 2

At a pH of 8.5 a racemization occurs on the strongly acidic cation exchanger Amberlite IR-122 analytical grade (16 ml gel volume, Serva, Heidelberg) neither at 3.0 ml/min nor at 0.3 ml/min. The reference examples show that anion exchange groups are necessary for the reaction.

EXAMPLE 13

The racemization of D-5-IMH on liquid anion exchangers was investigated using tertiary and quaternary ammonium compounds.

The racemization of D-5-IMH is followed on-line in a polarimeter cell (5 ml volume) thermostated at 37° C. 4 ml substrate solution (0.2 g D-5-IMH in 1000 ml 0.05M glycine buffer (Na+, pH 8.5)) are combined with 1 ml distilled H₂O (blank batch) and with an aqueous solution of a tertiary (2) or quaternary ammonium compound (3, 4) (double batch) which had been adjusted with NaOH to a pH of likewise 8.5. The racemization was followed for at least 24 hours. The following were tested as additives:

1. Distilled H₂O (blank batch)
2. Triethanolamine (0.5M)
3. Hexadecyltrimethylammonium bromide (0.05M) ("cetyltrimethylammonium bromide")
4. Tetrabutylammonium hydrogen sulfate (0.5M)

Whereas triethanolamine brought about no (1.2%/h) and tetrabutylammonium hydrogen sulfate a slightly more rapid (1.8%/h) conversion than the blank value (1.2%/h), hexadecyltrimethylammonium bromide exhibits a more rapid racemization (4.3%/h) already at a tenth of the concentration of the other substances.

The difference between the two quaternary ammonium compounds (hexadecyltrimethylammonium bromide and tetrabutylammonium hydrogen sulfate) can possibly be explained by a stronger shielding of the positive charge in the symmetric compound.

What is claimed is:

1. A method for the racemization of 5-monosubstituted hydantoins having the following formula

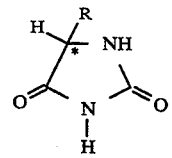

wherein * signifies a center of symmetry at which the racemization takes place and R is a proteinogenic or nonproteinogenic amino acid, which consists essentially of reacting the hydantoin to be racemized with an organic anionic exchanger in water or a buffer system which is at a pH in the range of 6–13.5 and which is suitable to effect racemization of the hydantoin.

2. The method according to claim 1 in which an ion exchanger with quaternary ammonium groups.

3. The method according to any one of claims 1 or 2 in which the reaction temperature is in a range from 0°–100° C.

4. The method according to any one of claims 1 or 3 which is carried out in a buffer system.

5. The method according to claim 4 in which the method is carried out in a glycine buffer.

6. The method according to any one of claims 1 or 3 in which the hydantoin to be racemized is used in a concentration between 0.1–250 g/l.

7. The method according to any one of claims 1 or 3 including the step of enzymaticaly splitting an enantiomer of the racemized hydantoin to an enantiomericaly pure L- or D-amino acid.

* * * * *